United States Patent [19]
Seaburn

[11] Patent Number: 6,084,662
[45] Date of Patent: Jul. 4, 2000

[54] LIGHT TRANSMITTANCE MEASURING DEVICE AND PROCESS FOR SEPARATING TRANSMITTANCE AND REFLECTANCE

[76] Inventor: Scott K. Seaburn, 300 Kahelu Ave., Suite 35, Mililani, Hi. 96789

[21] Appl. No.: 08/766,729

[22] Filed: Dec. 13, 1996

[51] Int. Cl.[7] .................................................. G01N 21/00
[52] U.S. Cl. .............................. 356/73; 356/432; 356/445
[58] Field of Search .............................. 356/73, 244, 432, 356/445; 250/559.11, 559.4, 215, 216, 578.1, 239

[56] References Cited

U.S. PATENT DOCUMENTS 4,125,328  11/1978  Suga ........................................... 356/73

Primary Examiner—Frank G. Font
Assistant Examiner—Reginald A. Ratliff
Attorney, Agent, or Firm—Martin E. Hsia

[57] ABSTRACT

A device for measuring transmittance through a material in which a detector and a light source are mounted in a single housing and light emitted from the light source is transmitted through the material and then retro-reflected by a retro-reflector into the light detector.

11 Claims, 1 Drawing Sheet

LIGHT TRANSMITTANCE MEASURING DEVICE AND PROCESS FOR SEPARATING TRANSMITTANCE AND REFLECTANCE

TECHNICAL FIELD

This invention provides an improved light transmittance meter and method for measuring transmissivity and/or reflectance of glass or other materials either individually or simultaneously.

BACKGROUND ART

The normal method for making transmissivity measurements uses a light source on one side of the material to be tested and a detector on the other side. This emitter (light source) and detector combination is calibrated by first taking a measurement without anything between these two components. A piece of glass or other material to be tested is placed between the emitter and detector and the corresponding transmissivity can be derived from the ratio of the measured value to the calibration value. This may be a ratio of voltages or currents depending on the circuit configuration of the detector.

DISCLOSURE OF INVENTION

The invention herein described makes use of a retro-reflective material to make transmissivity and reflectance measurements. A retro-reflector has the property that the reflected light returns along the incident path back toward the source, as contrasted with a reflector, such as a mirror, that reflects light at an incident angle away from the source. The meter part of the invention consists of a light source, detector and optical components contained in the same enclosure and oriented in such a way as to separate transmissivity and reflectivity measurements.

The separation of the transmissivity and reflectivity measurements is accomplished by the positioning of the optics, including the light source, detector, beamsplitter and lenses. This configuration is shown in FIG. 1.

By directing the light source at the test material at an angle A other than the normal (90 degrees), the reflection from the surfaces of the glass or test material returns along a different path than the light returned from the retro-reflector. By positioning detectors at points within the return path of the reflected light and the retro-reflected light both transmission and reflection can be measured.

The meter is calibrated for transmissivity measurements without any material between the retro-reflector and the meter. This value corresponds to 100% transmittance. This value is retained and used as the denominator of the ratio between the measured value and the calibration value (100% reading).

The advantage of this arrangement is the ability to have all the electronics in one unit and a passive retro-reflector. Another advantage is the ability to make simultaneous measurements of transmissivity and reflectivity; and for materials with specular reflections, the absorption can be derived.

BEST MODE FOR CARRYING OUT INVENTION

Figure 1:
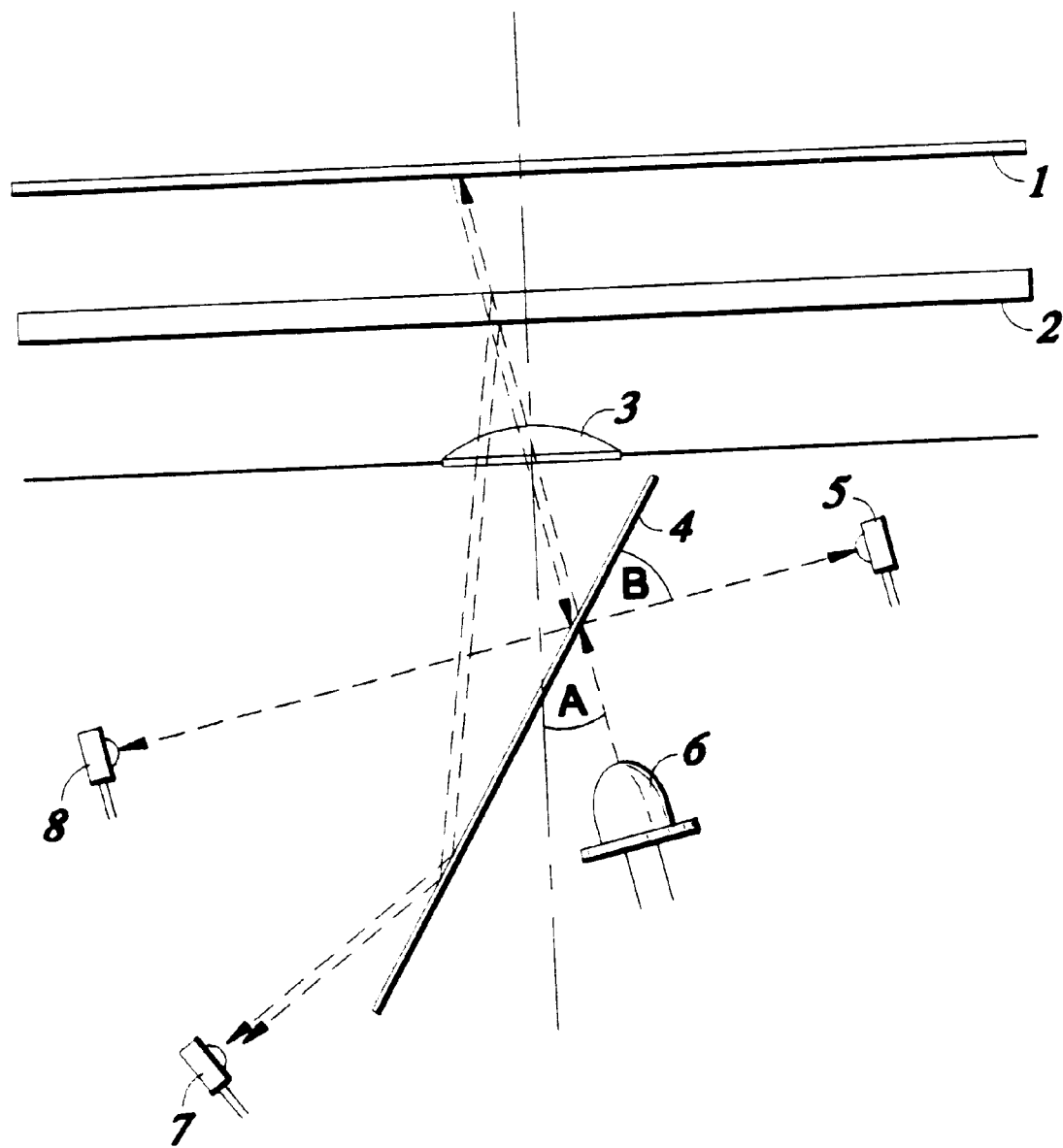
FIG. 1 is a sketch showing the orientation of the optical components of the invention.

The preferred embodiment of the invention makes use of a retro-reflective material 1 such as those manufactured by 3M Corporation. The meter contains an optical assembly that aims the light source 6 at the reflector 1 at an angle A less than 90 degrees from the normal, preferably less than 60 degrees, and optimally less than 20 degrees. A beam splitter 4 is positioned in front of the source and at an angle of approximately 45 degrees between the source 6 and the detector 8. A collimating lens 3 positioned at the front of the assembly serves to minimize the effects of distance or thickness of the glass 2 on the measurement. An additional detector 5 is positioned to monitor the strength of the light source 6 to maintain calibration as the light intensity varies due to temperature or aging. The light received at the primary detector 8 measures the retro-reflected light and the reflection detector 7 measures the specular reflected light.

INDUSTRIAL APPLICABILITY

This invention can be used to measure the transmissivity and/or reflectivity of glass or other translucent material.

What is claimed is:

1. A device for measuring transmissivity of a material, comprising:
    a retro-reflector;
    a housing;
    a light source mounted in said housing;
    a transmissivity light detector mounted in said housing, whereby light emitted from said light source is transmitted through said material onto said retro-reflector, and then is retro-reflected by said retro-reflector into said transmissivity light detector; and
    a reflectivity light detector mounted in said housing spaced apart from said transmissivity light detector, whereby light emitted from said light source is reflected by said material into said reflectivity light detector.

2. A device according to claim 1, further comprising:
    a beamsplitter mounted in said housing to split light emitted from said light source into a calibration beam and a source beam; and
    a calibration detector mounted in said housing to detect said calibration beam.

3. A device according to claim 2, further comprising:
    a collimating lens between said beamsplitter and said material.

4. A device according to claim 1, wherein said source beam is directed to said retro-reflector at an angle less than 60 degrees from normal.

5. A device according to claim 4, wherein said source beam is directed to said retro-reflector at an angle less than 20 degrees from normal.

6. A process for measuring transmittance of a material, comprising:
    emitting light from a light source;
    retro-reflecting said light from a retro-reflector to form a retro-reflected measurement beam;
    measuring the strength of said retro-reflected measurement beam;
    inserting said material between said light source and said retro-reflector;
    emitting light from said light source through said material to form a transmitted light;
    retro-reflecting said transmitted light from said retro-reflector to form a retro-reflected transmissivity beam;
    measuring the strength of said retro-reflected transmissivity beam; and
    comparing the relative strengths of said measurement beam and said transmissivity beam;

simultaneously measuring the strength of light reflected from said material.

7. A process according to claim 6, further comprising:

splitting said light from said light source into a source beam and a calibration beam;

monitoring the strength of said calibration beam to maintain calibration of said light source.

8. A process according to claim 6, further comprising:

collimating said light emitted from said light source.

9. A process according to claim 6, wherein said transmitted light defines an incident angle from a direction normal to said retro-reflector.

10. A process according to claim 9, wherein said incident angle is less than 60 degrees.

11. A process according to claim 10, wherein said incident angle is less than 20 degrees.

* * * * *